US007927795B2

(12) United States Patent
Santin

(10) Patent No.: US 7,927,795 B2
(45) Date of Patent: *Apr. 19, 2011

(54) GENE EXPRESSION PROFILING IN PRIMARY OVARIAN SEROUS PAPILLARY TUMORS AND NORMAL OVARIAN EPITHELIUM

(75) Inventor: Alessandro D. Santin, Little Rock, AR (US)

(73) Assignee: Board of Trustees of the University of Arkansas, Little Rock, AK (US)

( * ) Notice: Subject to any disclaimer, the term of this patent is extended or adjusted under 35 U.S.C. 154(b) by 229 days.

This patent is subject to a terminal disclaimer.

(21) Appl. No.: 10/862,517

(22) Filed: Jun. 7, 2004

(65) Prior Publication Data

US 2005/0048535 A1    Mar. 3, 2005

Related U.S. Application Data

(60) Provisional application No. 60/476,934, filed on Jun. 9, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6; 435/91.2; 435/287.2; 536/23.1; 536/24.3; 977/792

(58) Field of Classification Search .................. None
See application file for complete search history.

(56) References Cited

OTHER PUBLICATIONS

Lu, K.H. et al., Clin. Cancer Res., vol. 10, pp. 3291-3300 (2004).*
Hibbs, K. et al., Am. J. Pathol., vol. 165, pp. 397-414 (2004).*
Zorn, K. et al., Clin. Cancer Res., vol. 11, pp. 6422-6430 (2005).*
Meinhold-Heerlein, I. et al., Oncogene, vol. 24, pp. 1053-1065 (2005).*
Donninger, H. et al., Oncogene, vol. 23, pp. 8065-8077 (2004).*
Olivier, R.I. et al, Eur. J. Cancer, vol. 42, pp. 2930-2938 (2006).*
Zorn, K. et al., Clin. Cancer Res., vol. 9, pp. 4811-4818 (2003).*
OMIM Database, PAI2, downloaded Oct. 28, 2009.*
Hough, C.D. et al., Cancer Res., vol. 60, pp. 6281-6287 (2000).*
Sawiris et al., Cancer Res., vol. 62, pp. 2923-2928 (2002).*

* cited by examiner

*Primary Examiner* — Teresa E Strzelecka
(74) *Attorney, Agent, or Firm* — Benjamin Aaron Adler

(57) ABSTRACT

Gene expression profiling and hierarchal clustering analysis readily distinguish normal ovarian epithelial cells from primary ovarian serous papillary carcinomas. Laminin, tumor-associated calcium signal transducer 1 and 2 (TROP-1/EpCAM; TROP-2), claudin 3, claudin 4, ladinin 1, S100A2, SERPIN2 (PAI-2), CD24, lipocalin 2, osteopontin, kallikrein 6 (protease M), kallikrein 10, matriptase and stratifin were found among the most highly overexpressed genes in ovarian serous papillary carcinomas, whereas transforming growth factor beta receptor III, platelet-derived growth factor receptor alpha, SEMACAP3, ras homolog gene family, member I (ARHI), thrombospondin 2 and disabled-2/differentially expressed in ovarian carcinoma 2 (Dab2/DOC2) were significantly down-regulated. Therapeutic strategy targeting TROP-1/Ep-CAM by monoclonal chimeric/humanized antibodies may be beneficial in patients harboring chemotherapy-resistant ovarian serous papillary carcinomas.

6 Claims, 5 Drawing Sheets

GENE EXPRESSION PROFILING IN PRIMARY OVARIAN SEROUS PAPILLARY TUMORS AND NORMAL OVARIAN EPITHELIUM

CROSS-REFERENCE TO RELATED APPLICATION

This non-provisional patent application claims benefit of provisional patent application U.S. Ser. No. 60/476,934, filed Jun. 9, 2003, now abandoned.

BACKGROUND OF THE INVENTION

1. Field of the Invention

The present invention relates generally to the field of cancer research. More specifically, the present invention relates to gene expression profiling between primary ovarian serous papillary tumors and normal ovarian epithelium.

2. Description of the Related Art

Ovarian carcinoma remains the cancer with the highest mortality rate among gynecological malignancies with 25,400 new cancer cases estimated in 2003 in the United States alone. Ovarian serous papillary cancer (OSPC) represents the most common histological type of ovarian carcinoma ranging from 45 to 60% of all epithelial ovarian tumors. Because of the insidious onset of the disease and the lack of reliable screening tests, two thirds of patients have advanced disease when diagnosed, and although many patients with disseminated tumors respond initially to standard combinations of surgical and cytotoxic therapy, nearly 90 percent will develop recurrence and inevitably succumb to their disease. Understanding the molecular basis of ovarian serous papillary cancer may have the potential to significantly refine diagnosis and management of these serous tumors, and may eventually lead to the development of novel, more specific and more effective treatment modalities.

cDNA microarray technology has recently been used to identify genes involved in ovarian carcinogenesis. Gene expression fingerprints representing large numbers of genes may allow precise and accurate grouping of human tumors and may have the potential to identify patients who are unlikely to be cured by conventional therapy. Consistent with this view, evidence has been provided to support the notion that poor prognosis B cell lymphomas and biologically aggressive breast and ovarian carcinomas can be readily separated into different groups based on gene expression profiles. In addition, large scale gene expression analysis have the potential to identify a number of differentially expressed genes in ovarian serous papillary tumor cells compare to normal ovarian epithelial cells and may therefore lay the groundwork for future studies testing some of these markers for clinical utility in the diagnosis and, eventually, the treatment of ovarian serous papillary cancer.

Because of the lack of an effective ovarian cancer screening program and the common development of chemotherapy resistant disease after an initial response to cytotoxic agents (i.e., platinum based regimen), ovarian cancer remains the most lethal among the gynecologic malignancies. Thus, the identification of novel ovarian tumor markers to be used for early detection of the disease as well as the development of effective therapy against chemotherapy resistant/recurrent ovarian cancer remains a high priority.

The prior art is deficient in understanding the molecular differences between ovarian serous papillary cancer cells and normal ovarian epithelium. The present invention fulfills this need in the art by providing gene expression profiling for these two types of tissues.

SUMMARY OF THE INVENTION

The present invention identifies genes with a differential pattern of expression between ovarian serous papillary carcinomas (OSPC) and normal ovarian epithelium and uses this knowledge to develop novel diagnostic and therapeutic marker for the treatment of this disease. Oligonucleotide microarrays with probe sets complementary to 12,533 genes were used to analyze gene expression profiles of ten primary ovarian serous papillary carcinomas cell lines, two established ovarian serous papillary cancer cell lines (i.e., UCI-101, UCI-107) and five primary normal ovarian epithelium cultures (NOVA). Unsupervised analysis of gene expression data identified 129 and 170 genes that exhibited >5-fold up-regulation and down-regulation respectively in primary ovarian serous papillary carcinomas compared to normal ovarian epithelium. Genes overexpressed in established ovarian serous papillary carcinomas cell lines were found to have little correlation to those overexpressed in primary ovarian serous papillary carcinomas, highlighting the divergence of gene expression that occur as the result of long-term in vitro growth.

Hierarchal clustering of the expression data readily distinguished normal tissue from primary ovarian serous papillary carcinomas. Laminin, claudin 3 and claudin 4, tumor-associated calcium signal transducer 1 and 2 (TROP-1/Ep-CAM; TROP-2), ladinin 1, S100A2, SERPIN2 (PAI-2), CD24, lipocalin 2, osteopontin, kallikrein 6 (protease M) and kallikrein 10, matriptase (TADG-15) and stratifin were found among the most highly overexpressed gene in ovarian serous papillary carcinomas compared to normal ovarian epithelium. Down-regulated genes in ovarian serous papillary carcinomas included transforming growth factor beta receptor III, platelet-derived growth factor receptor alpha, SEMACAP3, ras homolog gene family member I (ARHI), thrombospondin 2 and disabled-2/differentially expressed in ovarian carcinoma 2 (Dab2/DOC2). Differential expression of some of these genes including claudin 3 and claudin 4, TROP-1 and CD24 was validated by quantitative RT-PCR as well as by flow cytometry. Immunohistochemical staining of formalin fixed paraffin embedded tumor specimens from which primary ovarian serous papillary carcinomas cultures were derived further confirmed differential expression of CD24 and TROP-1/Ep-CAM markers on ovarian serous papillary carcinomas vs normal ovarian epithelium. These results, obtained from highly purified primary cultures of ovarian cancer, highlight important molecular features of ovarian serous papillary carcinomas and provide a foundation for the development of new type-specific therapies against this disease. For example, a therapeutic strategy targeting TROP-1/Ep-CAM by monoclonal chimeric/humanized antibodies may be beneficial in patients harboring chemotherapy-resistant ovarian serous papillary carcinomas.

The present invention is drawn to a method of detecting ovarian serous papillary carcinoma based on overexpression of a group of genes listed in Table 2.

In another embodiment, the present invention provides a method of detecting ovarian serous papillary carcinoma based on down-regulation of a group of genes listed in Table 3.

In another embodiment, the present invention provides a method of treating ovarian serous papillary carcinoma by inhibiting the expression and function of tumor-associated calcium signal transducer 1 (TROP-1/Ep-CAM) gene.

In another embodiment, the present invention provides a method of treating ovarian serous papillary carcinoma by delivering *Clostridium perfringens* enterotoxins to ovarian tumor cells overexpressing claudin 3 or claudin 4 protein.

Other and further aspects, features, and advantages of the present invention will be apparent from the following description of the presently preferred embodiments of the invention. These embodiments are given for the purpose of disclosure.

DETAILED DESCRIPTION OF THE INVENTION

Figure 1:
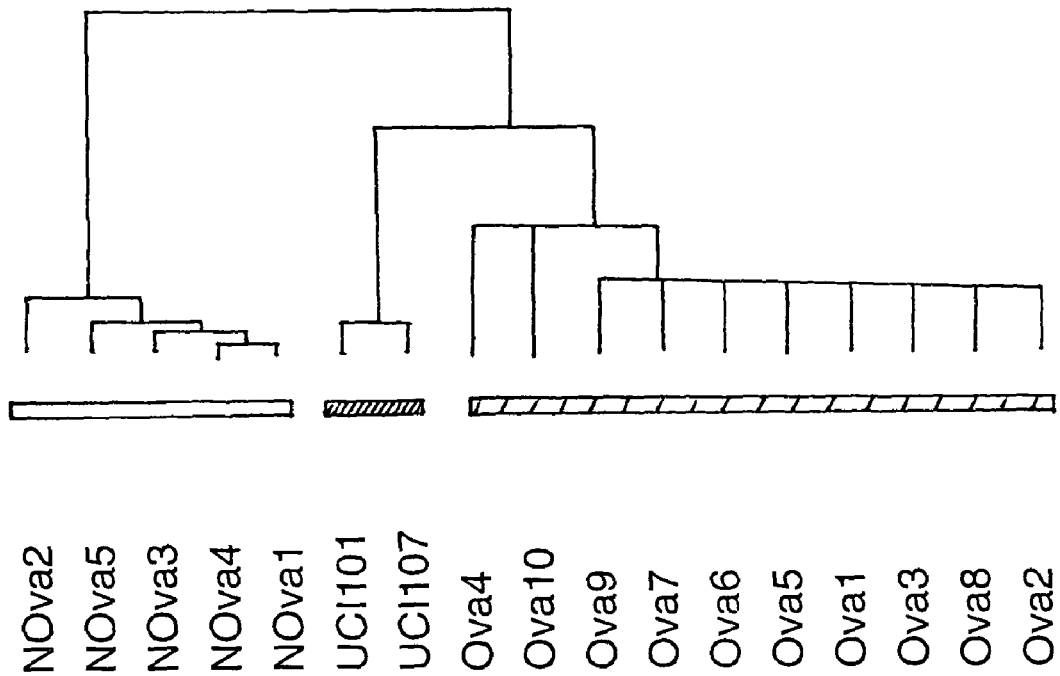
FIG. 1 shows hierarchical clustering of 15 primary ovarian cell lines (i.e., 10 ovarian serous papillary carcinomas lines and 5 normal ovarian epithelial cell lines) and two established ovarian serous papillary carcinomas cell lines (i.e., UCI-101 and UCI-107).

High-throughput technologies for assaying gene expression, such as high-density oligonucleotide and cDNA microarrays, may offer the potential to identify clinically relevant gene highly differentially expressed between ovarian tumors and normal control ovarian epithelial cells. This report discloses a genome-wide examination of differential gene expression between primary ovarian serous papillary carcinomas and normal ovarian epithelial cells (NOVA). Short-term primary ovarian serous papillary carcinomas and normal ovarian epithelial cells cultures were used to minimize the risk of a selection bias inherent in any long term in vitro growth. In the present invention, only the cancer cells derived from papillary serous histology tumors, which is the most common histological type of ovarian cancer, were included to limit the complexity of gene expression analysis.

Hierarchical clustering of the samples and gene expression levels within the samples led to the unambiguous separation of ovarian serous papillary carcinomas from normal ovarian epithelial cells. Of interest, the expression patterns detected in primary ovarian serous papillary carcinomas cells were consistently different from those seen in established serous papillary ovarian carcinoma cell lines (i.e., UCI-101 and UCI-107). These data thus highlight the divergence of gene expression that occur as a result of long-term in vitro growth. Furthermore, these data emphasize that although established ovarian cancer cell lines provide a relatively simple model to examine gene expression, primary ovarian serous papillary carcinomas and normal ovarian epithelial cells cultures represent better model systems for comparative gene expression analysis. Because of these results, the present invention was limited to analysis of differential gene expression between the two homogeneous groups of primary ovarian serous papillary carcinomas and normal ovarian epithelial cells.

The present invention detected 298 genes that have at least five-fold difference in expression levels between ovarian serous papillary carcinomas and normal ovarian epithelial cells. The known function of some of these genes may provide insight into the biology of serous ovarian tumors while others may prove to be useful diagnostic and therapeutic markers against ovarian serous papillary carcinomas.

Laminin Gamma 2

Laminin gamma 2 gene was found to be the most highly differentially expressed gene in ovarian serous papillary carcinomas with over 46-fold up-regulation relative to normal ovarian epithelial cells. Cell migration of ovarian tumor cells is considered essential for cell dissemination and invasion of the submesothelial extracellular matrix commonly seen in ovarian cancer. The laminin gamma 2 isoform has been previously suggested to play an important role in tumor cell adhesion, migration, and scattering of ovarian carcinoma cells. Thus, in agreement with recent reports in other human tumor, it is likely that high laminin expression by ovarian tumor cells may be a marker correlated with the invasive potential of ovarian serous papillary carcinomas. Consistent with this view, increased cell surface expression of laminin was found in highly metastatic tumors cells compared to cells of low metastatic potential. Importantly, previous work has shown that attachment and metastases of tumor cells can be inhibited by incubation with anti-laminin antibodies or synthetic laminin peptides.

TROP-1/Ep-CAM

TROP-1/Ep-CAM (also called 17-1A, ESA, EGP40) is a 40 kDa epithelial transmemebrane glycoprotein found to be overexpressed in normal epithelia cells and in various carcinomas including colorectal and breast cancer. In most adult epithelial tissues, enhanced expression of Ep-CAM is closely associated with either benign or malignant proliferation. Because among mammals Ep-CAM is an evolutionary highly conserved molecule, this seem to suggest an important biologic function of this molecule in epithelial cells and tissue. In this regard, Ep-CAM is known to function as an intercellular adhesion molecule and could have a role in tumor metastasis. Because a randomized phase II trial with mAb CO17-1A in colorectal carcinoma patients has demonstrated a significant decrease in recurrence and mortality in mAb-treated patients versus control patients, TROP-1/Ep-CAM antigen has attracted substantial attention as a target for immunotherapy for treating human carcinomas. Importantly, data disclosed herein showed that TROP-1/Ep-CAM was overexpressed 39-folds in ovarian serous papillary carcinomas compared to normal ovarian epithelial cells. These data provide support for the notion that anti-Ep-CAM antibody therapy may be a novel, and potentially effective treatment option for ovarian serous papillary carcinomas patients with residual/resistant disease after surgical and cytotoxic therapy. Protein expression data obtained by flow cytometry on primary ovarian serous papillary carcinomas cell lines and by immunohistochemistry on uncultured ovarian serous papillary carcinomas blocks support this view.

Claudin 3 And Claudin 4

Claudin 3 and claudin 4, two members of claudin family of tight junction proteins, were two of the top five differentially expressed genes in ovarian serous papillary carcinomas. These results are consistent with a previous report on gene expression in ovarian cancer. Although the function of claudin proteins in ovarian cancer is still unclear, these proteins likely represent a transmembrane receptor. Of interest, claudin-3 and claudin 4 are homologous to CPE-R, the low and high-affinity intestinal epthelial receptor for *Clostridium Perfringens* enterotoxin (CPE), respectively, and are sufficient to mediate *Clostridium Perfringens* enterotoxin binding and trigger subsequent toxin-mediated cytolysis. These known functions of claudin-3 and claudin-4, combined with their extremely high level of expression in ovarian serous papillary carcinomas suggest a potential use of *Clostridium Perfringens* enterotoxin as a novel therapeutic strategy for the treatment of chemotherapy resistant disease in ovarian cancer patients. Supporting this view, functional cytotoxicity of *Clostridium Perfringens* enterotoxin in metastatic androgen-independent prostate cancer overexpressing claudin-3 has recently been reported.

Plasminogen Activator Inhibitor-2 (PAI-2)

Plasminogen activator inhibitor-2 (PAI-2), a gene whose expression has been linked to cell invasion in several human malignancies as well as to protection from tumor necrosis factor-a (TNF-a)-mediated apoptosis, was overexpressed 12-folds in ovarian serous papillary carcinomas compared to normal ovarian epithelial cells. Previous studies have shown that elevated levels of plasminogen activator inhibitor-2 are detectable in the ascites of ovarian cancer patients and that high plasminogen activator inhibitor-2 levels are independently predictive of a poor disease-free survial. Interestingly, in some of these studies, a 7-fold increase in plasminogen activator inhibitor-2 content was found in the omentum of ovarian cancer patients compared to the primary disease suggesting that metastatic tumors may overexpressed plasminogen activator inhibitor-2. Other studies, however, have identified plasminogen activator inhibitor-2 production as a favorable prognostic factor in epithelial ovarian cancer. Indeed, high PAI-2 expression in invasive ovarian tumors was limited to a group of ovarian serous papillary carcinomas patients who experience a more prolonged disease free and overall survival. The reason of these differences are not clear, but, as previously suggested, they may be related at least in part to the actions of macrophage colony stimulating factor-1 (CSF-1), a cytokine which has been shown to stimulate the release of PAI-2 by ovarian cancer cells.

CD24

CD24 is a small heavily glycosylated glycosylphosphatidylinositol-linked cell surface protein expressed in hematological malignancies as well as in a large variety of solid tumors. However, it is only recently that CD24 expression has been reported at RNA level in ovarian cancer. Consistent with this recent report, the present study shows that CD24 gene was overexpressed 14-folds in ovarian serous papillary carcinomas compared to normal ovarian epithelial cells. Because CD24 is a ligand of P-selectin, an adhesion receptor on activated endothelial cells and platelets, its expression may contribute to the metastatic capacities of CD24-expressing ovarian tumor cells. Importantly, because CD24 expression has been reported as an independent prognostic marker for ovarian cancer patients survival, it is likely that this marker delineating aggressive ovarian cancer disease may have therapeutic and/or diagnostic potential.

Lipocalin-2

Among the overexpressed genes identified herein, lipocalin 2 has not been previously linked to ovarian cancer. Lipocalin-2 represents a particularly interesting marker because of several features. Lipocalins are extracellular carriers of lipophilic molecules such as retinoids, steroids, and fatty acid, all of which may play important roles in the regulation of epithelial cells growth. In addition, because lipocalin is a secreted protein, it may play a role in the regulation of cell proliferation and survival. Of interest, two recent publications on gene expression profile of breast and pancreatic cancer have proposed lipocalin-2 as a novel therapeutic and diagnostic marker for prevention and treatment of these diseases. On the basis of the data disclosed herein, lipocalin 2 may be added to the known markers for ovarian cancer.

Osteopontin (SPP1)

Osteopontin (SPP1) is an acidic, calcium-binding glycophosphoprotein that has recently been linked to tumorigeneis in several experimental animal models and human patients studies. Because of its integrin-binding arginine-glycine-aspartate (RDG) domain and adhesive properties, osteopontin has been reported to play a crucial role in the metastatic process of several human tumors. However, it is only recently that upregulated expression of osteopontin in ovarian cancer has been identified. Importantly, because of the secreted nature of this protein, osteopontin has been proposed as a novel biomarkers for the early recognition of ovarian cancer. In the data disclosed herein, SPP1 gene was overexpressed 10-folds in ovarian serous papillary carcinomas compared to normal ovarian epithelial cells. Taken together, these data confirm a high expression of osteopontin in ovarian serous papillary carcinomas and it is of interest to further assess its clinical usefulness in ovarian cancer.

Kallikreins

The organization of kallikreins, a gene family consisting of 15 genes that all encode for trypsin-like or chymotrypsin-like serine proteases, has been recently elucidated. Serine proteases have well characterized roles in diverse cellular activities, including blood coagulation, wound healing, digestion, and immune responses, as well as tumor invasion and metastasis. Importantly, because of the secreted nature of some of these enzymes, prostate-specific antigen (PSA) and kallikrein 2 have already found important clinical application as prostate cancer biomarkers. Of interest, kallikrein 10, kallikrein 6 (also known as zyme/protease M/neurosin), and matriptase (TADG-15/MT-SP1) were all found highly expressed in ovarian serous papillary carcinomas compared to normal ovarian epithelial cells. These data confirm previous results showing high expression of several kallikrein genes and proteins in ovarian neoplasms. Moreover, these results obtained by high-throughput technologies for assaying gene expression further emphasize the view that some members of the kallikrein family have the potential to become novel ovarian cancer markers for ovarian cancer early diagnosis as well as targets for novel therapies against recurrent/refractory ovarian disease.

Other highly overexpressed genes in ovarian serous papillary carcinomas include stratifin, desmoplakin, S100A2, cytokeratins 6 and 7, MUC-1, and MMP12.

Down-Regulated Genes

The present invention also identified a large number of down-regulated (at least 5-fold) genes in ovarian serous papillary carcinomas such as transforming growth factor beta receptor III, platelet-derived growth factor receptor alpha, SEMACAP3, ras homolog gene family member I (ARHI), thrombospondin 2 and disabled-2/differentially expressed in ovarian carcinoma 2 (Dab2/DOC2) (Table 3). Some of these genes encode well-known tumor suppressor genes such as SEMACAP3, ARHI, and Dab2/DOC2, while others encode for proteins important for ovarian tissue homeostasis or that have been previously implicated in apoptosis, proliferation, adhesion or tissue maintenance.

In conclusion, several ovarian serous papillary carcinomas restricted markers have been identified herein. Some of these genes have been previously reported to be highly expressed in ovarian cancer while others have not been previously linked with this disease. Identification of TROP-1/Ep-CAM as the second most highly overexpressed gene in ovarian serous papillary carcinomas suggests that a therapeutic strategy targeting TROP-1/Ep-CAM by monoclonal antibodies, an approach that has previously been shown to increase survival in patients harboring stage III colon cancer, may be also beneficial in patients harboring chemotherapy-resistant ovarian serous papillary carcinomas. Targeting claudin 3 and claudin 4 by local and/or systemic administration of Clostridium Perfringens enterotoxin may represent another novel therapeutic modalities in patients harboring ovarian serous papillary carcinomas refractory to standard treatment.

Thus, the present invention is drawn to a method of detecting ovarian serous papillary carcinoma. The method involves performing statistical analysis on the expression levels of a group of genes listed in Table 2. Examples of such genes include laminin, tumor-associated calcium signal transducer 1 (TROP-1/Ep-CAM), tumor-associated calcium signal transducer 2 (TROP-2), claudin 3, claudin 4, ladinin 1, S100A2, SERPIN2 (PAI-2), CD24, lipocalin 2, osteopontin, kallikrein 6 (protease M), kallikrein 10, matriptase and stratifin. Over-expression of these genes would indicate that such individual has ovarian serous papillary carcinoma. In general, gene expression can be examined at the protein or RNA level. Preferably, the examined genes have at least a 5-fold over-expression compared to expression in normal individuals. In one embodiment, gene expression is examined by DNA microarray and the data are analyzed by the method of hierarchical cluster analysis. In another embodiment, gene expression is determined by flow cytometric analysis or immunohistochemical staining.

The present invention also provides a method of detecting ovarian serous papillary carcinoma based on down-regulation of a group of genes listed in Table 3. Examples of such genes include transforming growth factor beta receptor III, platelet-derived growth factor receptor alpha, SEMACAP3, ras homolog gene family, member I (ARHI), thrombospondin 2 and disabled-2/differentially expressed in ovarian carcinoma 2 (Dab2/DOC2). In general, gene expression can be examined at the protein or RNA level. Preferably, the examined genes have at least a 5-fold down-regulation compared to expression in normal individuals. In one embodiment, gene expression is examined by DNA microarray and the data are analyzed by the method of hierarchical cluster analysis. In another embodiment, gene expression is determined by flow cytometric analysis or immunohistochemical staining.

In another aspect of the present invention, there is provided a method of treating ovarian serous papillary carcinoma by inhibiting the expression and function of tumor-associated calcium signal transducer 1 (TROP-1/Ep-CAM) gene. In general, inhibition of gene expression can be obtained using anti-TROP-1/Ep-CAM antibody or anti-sense oligonucleotide according to protocols well known in the art. For example, monoclonal anti-TROP-1/Ep-CAM (chimeric/humanized) antibody can be used in antibody-directed therapy that has improved survival of patients described previously (Riethmuller et al., 1998).

In another embodiment, there is provided a method of treating ovarian serous papillary carcinoma by delivering Clostridium perfringens enterotoxins to ovarian tumor cells overexpressing claudin 3 or claudin 4 protein. Preferably, the enterotoxins are delivered by systemic administration, intraperitoneal administration or intratumoral injection.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Establishment of Primary Ovarian Serous Papillary Carcinoma and Normal Ovarian Epithelial Cell Lines A total of 15 primary cell lines (i.e., 10 ovarian serous papillary carcinomas cell lines and 5 normal ovarian epithelial cell lines) were established after sterile processing of the tumor samples from surgical biopsies as previously described for ovarian carcinoma specimens (Ismail et al., 2000; Hough et al., 2000; Santin et al., 2000). UCI-101 and UCI-107, two previously characterized ovarian serous papillary carcinomas cell lines (Fuchtneretal., 1993; Gamboa et al., 1995) were also included in the analysis. Tumors were staged according to the F.I.G.O. operative staging system. Radical tumor debulking, including a total abdominal hysterectomy and omentectomy, was performed in all ovarian carcinoma patients while normal ovarian tissue was obtained from consenting donors who undergo surgery for benign pathology scraping epithelial cells from the ovarian surface. No patient received chemotherapy before surgical therapy. The patient and donors characteristics are described in Table 1.

Briefly, normal tissue was obtained by scraping epithelial cells from the ovarian surface and placing cells in RPMI 1640 medium (Sigma Chemical Co., St. Louis, Mo.) containing 10% fetal bovine serum (FBS, Invitrogen, Grand Island, N.Y.), 200 U/ml penicillin, and 200 µg/ml streptomycin. The epithelial explants were then allowed to attach and proliferate. Once the epithelial cells reached confluency, explants were trypsinized and subcultured for 3 to 4 passages before being collected for RNA extraction.

Viable tumor tissue was mechanically minced in RPMI 1640 to portions no larger than 1-3 mm$^3$ and washed twice with RPMI 1640. The portions of minced tumor were then placed into 250 ml flasks containing 30 ml of RPMI 1640 enzyme solution containing 0.14% collagenase Type I (Sigma, St. Louis, Mo.) and 0.01% DNAse (Sigma, 2000 KU/mg), and incubated on a magnetic stirring apparatus overnight at 4° C. Enzymatically dissociated tumor was then filtered through 150 mm nylon mesh to generate single cell suspension. The resultant cell suspension was then washed twice in RPMI 1640 plus 10% fetal bovine serum (FBS, Invitrogen, Grand Island, N.Y.). Primary cell lines were maintained in RPMI 1640 supplemented with 10% FBS, 200 U/ml penicillin, and 200 µg/ml streptomycin at 37° C., 5% $CO_2$ in 75-150 cm² tissue culture flasks (Corning Inc., Corning, N.Y.). Tumor cells were collected for RNA extraction at a confluence of 50% to 80% after a minimum of two to a maximum of twelve passages in vitro. The epithelial nature and the purity of ovarian serous papillary carcinomas and normal ovarian epithelial cells cultures were verified by immunohistochemical staining and flow cytometric analysis with antibodies against cytokeratin as previously described (Ismail et al., 2000; Santin et al., 2000). Only primary cultures which had at least 90% viability and contained >99% epithelial cells were used for total RNA extraction.

TABLE 1

Characteristics of The Patients

| Patient | Age | Race | Grade | Chemotherapy regimen | Stage |
|---|---|---|---|---|---|
| OSPC 1 | 42 | White | G2/3 | TAX + CARB | IV A |
| OSPC 2 | 67 | White | G3 | TAX + CARB | III B |
| OSPC 3 | 61 | White | G3 | TAX + CARB | III C |
| OSPC 4 | 60 | White | G3 | TAX + CARB | III C |
| OSPC 5 | 59 | Afro-American | G2/3 | TAX + CARB | III C |
| OSPC 6 | 72 | White | G3 | TAX + CARB | IV A |
| OSPC 7 | 63 | White | G3 | TAX + CARB | III C |
| OSPC 8 | 74 | Afro-American | G2/3 | TAX + CARB | III C |
| OSPC 9 | 68 | White | G3 | TAX + CARB | III B |
| OSPC 10 | 77 | White | G2/3 | TAX + CARB | III C |

OSPC, ovarian serous papillary carcinoma.

Example 2

Microarray Hybridization and Statistical Analysis

RNA purification, cDNA synthesis, cRNA preparation, and hybridization to the Affymetrix Human U95Av2 GeneChip microarray were performed according to the manufacturer's protocols and as reported (Zhan et al., 2002).

All data used in the analyses were derived from Affymetrix 5.0 software. GeneChip 5.0 output files are given as a signal that represents the difference between the intensities of the sequence-specific perfect match probe set and the mismatch probe set, or as a detection of present, marginal, or absent signals as determined by the GeneChip 5.0 algorithm. Gene arrays were scaled to an average signal of 1500 and then analyzed independently. Signal calls were transformed by the log base 2 and each sample was normalized to give a mean of 0 and variance of 1.

Statistical analyses of the data were performed with the software packages SPSS10.0 (SPSS, Chicago, Ill.) and the significance analysis of microarrays (SAM) method (Tusher et al., 2001). Genes were selected for analysis based on detection and fold change. In each comparison, genes having "present" detection calls in more than half of the samples in the overexpressed gene group were retained for statistical analysis if they showed >2-fold change between groups. Retained genes were subjected to SAM to establish a false discovery rate (FDR), then further filtered via the Wilcoxon rank sum (WRS) test at alpha=0.05. The false discovery rate (FDR) obtained from the initial SAM analysis was assumed to characterize genes found significant via WRS.

The hierarchical clustering of average-linkage method with the centered correlation metric was used (Eisen et al., 1998). The dendrogram was constructed with a subset of genes from 12,533 probe sets present on the microarray, whose expression levels vary the most among the 11 samples, and thus most informative. For the hierarchical clustering shown in FIG. 1 and FIG. 2, only genes significantly expressed and whose average change in expression level was at least two-fold were chosen. The expression value of each selected gene was re-normalized to have a mean of zero.

Example 3

Gene Expression Profiles Distinguish Ovarian Serous Papillary Carcinoma Cells from Normal Ovarian Epithelial Cells and Identify Differentially Expressed Genes Flash frozen biopsies from ovarian tumor tissue are known to contain significant numbers of contaminating stromal cells as well as a variety of host derived immune cells (e.g., monocytes, dendritic cells, lymphocytes). In addition, because ovarian epithelial cells represent a small proportion of the total cells found in the normal ovary, it is difficult to collect primary material that is free of contaminating ovarian stromal cells in sufficient quantities to conduct comparative gene expression analyses. Ovarian epithelial cells, however, can be isolated and expanded in culture for about 15 passages (Ismail et al., 2000; Hough et al., 2000) while the majority of primary ovarian carcinomas can be expanded in vitro for at least a few weeks (Santin et al., 2000). Thus, short term primary ovarian serous papillary carcinomas and normal ovarian epithelial cell cultures were used in the following studies.

Comprehensive gene expression profiles of 10 primary ovarian serous papillary carcinomas cell lines and 5 primary normal ovarian epithelial cell lines were generated using high-density oligonucleotide arrays with 12,533 probe sets, which in total interrogated some 10,000 genes. In addition, gene expression profiles derived from two established and previously characterized cell lines (UCI-101 and UCI-107) were also analyzed. By combining the detection levels of genes significantly expressed in primary and established ovarian serous papillary carcinomas cell lines, very little correlation between the two groups of cells was found. Indeed, as shown in FIG. 1, UCI-101 and UCI-107 established cell lines grouped together in the dendrogram while all 10 primary ovarian serous papillary carcinomas cell lines clustered tightly together in the rightmost columns separately by the 5 normal ovarian epithelial cell line controls. Because of these results, gene expression profile analysis was focused on the two homogeneous groups of primary ovarian serous papillary carcinomas cells and normal ovarian epithelial cells.

Using the nonparametric WRS test ($p<0.05$) that readily distinguished between the two groups of primary cultures, 1,546 genes were found to be differentially expressed between ovarian serous papillary carcinomas cells and normal ovarian epithelial cells. There were 365 genes showing >5-fold change along with "present" detection calls in more than half the samples in the overexpressed group. Of these, 350 were found significant by SAM, with a median FDR of 0.35% and a $90^{th}$ percentile FDR of 0.59%. Of the 365 aforementioned genes, 299 yielded $p<0.05$ via WRS, and 298 were among the genes found significant by SAM.

Figure 2:
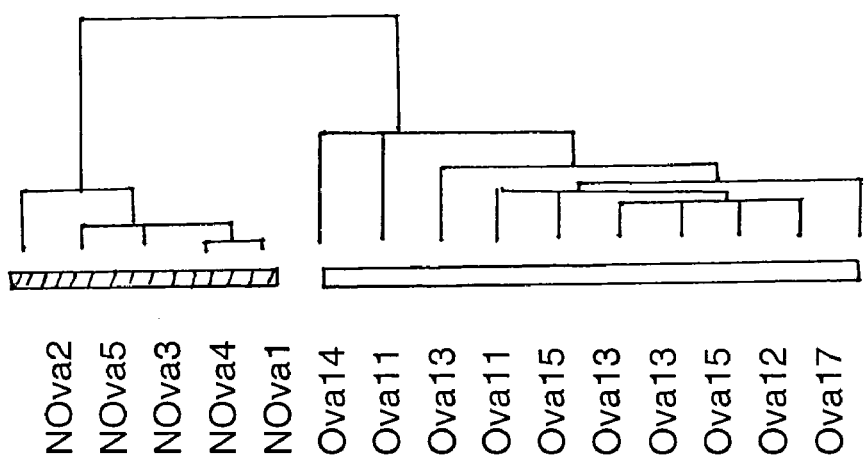
FIG. 2 shows molecular profile of 10 primary ovarian serous papillary carcinomas cell lines and 5 normal ovarian epithelial cell lines. Hierarchical clustering of 299 genes uses a 5-fold threshold (P<0.05). The cluster is color coded using red for up-regulation, green for down-regulation, and black for median expression. Agglomerative clustering of genes was illustrated with dendrograms.
Figure 2:

FIG. 2 describes the cluster analysis performed on hybridization intensity values for 298 gene segments whose average change in expression level was at least five-fold and which were found significant with both WRS test and SAM analysis. All 10 ovarian serous papillary carcinomas were grouped together in the rightmost columns. Similarly, in the leftmost columns all 5 normal ovarian epithelial cell cultures were found to cluster tightly together. The tight clustering of ovarian serous papillary carcinomas from normal ovarian epithelial cells was "driven" by two distinct profiles of gene expression. The first was represented by a group of 129 genes that were highly expressed in ovarian serous papillary carcinomas and underexpressed in normal ovarian epithelial cells (Table 2). Many genes shown previously to be involved in ovarian carcinogenesis are present on these lists, while others are novel in ovarian carcinogeneis. Included in this group of genes are laminin, claudin 3 and claudin 4, tumor-associated calcium signal transducer 1 and 2 (TROP-1/Ep-CAM; TROP-2), ladinin 1, S100A2, SERPIN2 (PAI-2), CD24, lipocalin 2, osteopontin, kallikrein 6 (protease M), kallikrein 10, matriptase (TADG-15) and stratifin (Table 2). Importantly, TROP-1/Ep-CAM gene, which encodes for a transmembrane glycoprotein previously found to be overexpressed in various carcinoma types including colorectal and breast and where antibody-directed therapy has resulted in improved survival of patients, was 39-fold differentially expressed in ovarian serous papillary carcinomas when compared to normal ovarian epithelial cells (Table 2).

The second profile was represented by 170 genes that were highly expressed in normal ovarian epithelial cells and underexpressed in ovarian serous papillary carcinomas (Table 3). Included in this group of genes are transforming growth factor beta receptor III, platelet-derived growth factor receptor alpha, SEMACAP3, ras homolog gene family, member I (ARHI), thrombospondin 2 and disabled-2/differentially expressed in ovarian carcinoma 2 (Dab 2/DOC2) (Table 3).

TABLE 2

Upregulated Genes Expressed At Least 5 Fold Higher In Ovarian Serous Papillary Carcinoma Compared With Normal Ovarian Epithelial Cells

| Probe Set | Gene Symbol | Score(d)(SAM) | p of WRS | Ratio OVA/NOVA |
|---|---|---|---|---|
| 35280_at | LAMC2 | 1.68927386 | 0.006 | 46.45 |
| 35276_at | CLDN4 | 1.734410451 | 0.015 | 43.76 |
| 33904_at | CLDN3 | 1.650076713 | 0.02 | 40.24 |
| 575_s_at | TACSTD1 | 1.705816336 | 0.02 | 39.36 |
| 32154_at | TFAP2A | 1.667038647 | 0.002 | 33.31 |
| 39015_f_at | KRT6E | 1.062629117 | 0.047 | 28.02 |
| 1713_s_at | CDKN2A | 1.137682905 | 0.015 | 26.96 |
| 41376_i_at | UGT2B7 | 0.939735032 | 0.047 | 24.81 |
| 38551_at | L1CAM | 1.151935363 | 0.008 | 24.66 |
| 291_s_at | TACSTD2 | 1.249487388 | 0.047 | 24.46 |
| 33282_at | LAD1 | 1.422481563 | 0.006 | 24.31 |
| 34213_at | KIBRA | 1.533570321 | 0.002 | 23.06 |
| 38489_at | HBP17 | 1.522882814 | 0.004 | 22.54 |
| 36869_at | PAX8 | 1.43906836 | 0.004 | 22.20 |
| 38482_at | CLDN7 | 1.307716566 | 0.027 | 20.01 |
| 37909_at | LAMA3 | 1.121654521 | 0.027 | 19.24 |
| 34674_at | S100A1 | 1.219106334 | 0.008 | 19.01 |
| 1620_at | CDH6 | 0.908193479 | 0.036 | 18.69 |
| 32821_at | LCN2 | 1.99990601 | 0.008 | 18.13 |
| 522_s_at | FOLR3 | 1.113781518 | 0.02 | 17.90 |
| 39660_at | DEFB1 | 0.837612681 | 0.036 | 17.34 |
| 2011_s_at | BIK | 1.594057668 | 0.006 | 17.23 |
| 41587_g_at | FGF18 | 0.965726983 | 0.02 | 17.10 |
| 36929_at | LAMB3 | 1.115590892 | 0.047 | 16.76 |
| 35726_at | S100A2 | 1.036576352 | 0.004 | 15.05 |
| 1887_g_at | WNT7A | 1.186990893 | 0.004 | 14.75 |
| 35879_at | GAL | 1.223278825 | 0.002 | 14.65 |
| 266_s_at | CD24 | 1.756569076 | 0.004 | 14.45 |
| 1108_s_at | EPHA1 | 1.242309171 | 0.006 | 14.36 |
| 37483_at | HDAC9 | 1.406744957 | 0.006 | 14.28 |
| 31887_at | — | 1.311220827 | 0.011 | 13.68 |
| 1788_s_at | DUSP4 | 1.22421987 | 0.003 | 13.65 |
| 32787_at | ERBB3 | 0.996784565 | 0.02 | 13.21 |
| 41660_at | CELSR1 | 1.634286803 | 0.004 | 13.11 |
| 33483_at | NMU | 1.100849065 | 0.004 | 13.04 |
| 31792_at | ANXA3 | 0.896090153 | 0.011 | 12.90 |
| 36838_at | KLK10 | 1.026306829 | 0.02 | 12.71 |
| 1585_at | ERBB3 | 1.102058608 | 0.011 | 12.51 |
| 1898_at | TRIM29 | 1.071987353 | 0.002 | 12.44 |
| 37185_at | SERPINB2 | 0.815945986 | 0.027 | 12.26 |

TABLE 2-continued

Upregulated Genes Expressed At Least 5 Fold Higher In Ovarian Serous Papillary Carcinoma Compared With Normal Ovarian Epithelial Cells

| Probe Set | Gene Symbol | Score(d)(SAM) | p of WRS | Ratio OVA/NOVA |
|---|---|---|---|---|
| 406_at | ITGB4 | 1.296194559 | 0.006 | 11.66 |
| 1914_at | CCNA1 | 0.936342778 | 0.011 | 11.21 |
| 977_s_at | CDH1 | 0.93637461 | 0.036 | 11.19 |
| 37603_at | IL1RN | 1.103624942 | 0.015 | 11.14 |
| 35977_at | DKK1 | 1.123240701 | 0.006 | 10.74 |
| 36133_at | DSP | 1.280269127 | 0.002 | 10.69 |
| 36113_s_at | TNNT1 | 1.269558595 | 0.002 | 10.19 |
| 1802_s_at | ERBB2 | 0.787465706 | 0.006 | 9.61 |
| 2092_s_at | SPP1 | 1.34315986 | 0.02 | 9.53 |
| 35699_at | BUB1B | 1.026388835 | 0.006 | 9.49 |
| 37554_at | KLK6 | 0.895036336 | 0.027 | 9.45 |
| 38515_at | BMP7 | 0.945367 | 0.027 | 9.32 |
| 34775_at | TSPAN-1 | 1.001195829 | 0.02 | 9.01 |
| 37558_at | IMP-3 | 1.023799379 | 0.011 | 8.99 |
| 38324_at | LISCH7 | 1.308000521 | 0.006 | 8.96 |
| 39610_at | HOXB2 | 1.355268631 | 0.006 | 8.64 |
| 572_at | TTK | 1.122796615 | 0.006 | 8.53 |
| 1970_s_at | FGFR2 | 1.022708001 | 0.02 | 8.30 |
| 160025_at | TGFA | 1.065272755 | 0.015 | 8.28 |
| 41812_s_at | NUP210 | 1.39287031 | 0.006 | 8.26 |
| 34282_at | NFE2L3 | 1.165273649 | 0.008 | 8.06 |
| 2017_s_at | CCND1 | 1.114984456 | 0.002 | 8.04 |
| 33323_r_at | SFN | 1.202433185 | 0.008 | 8.01 |
| 38766_at | SRCAP | 1.131917941 | 0.008 | 7.99 |
| 41060_at | CCNE1 | 1.151246634 | 0.006 | 7.97 |
| 39016_r_at | KRT6E | 0.973486831 | 0.008 | 7.91 |
| 31610_at | MAP17 | 1.0156502 | 0.027 | 7.81 |
| 2027_at | S100A2 | 0.941919001 | 0.008 | 7.76 |
| 418_at | MKI67 | 0.826426448 | 0.011 | 7.46 |
| 1536_at | CDC6 | 1.08868941 | 0.017 | 7.37 |
| 634_at | PRSS8 | 0.899891713 | 0.02 | 7.30 |
| 34342_s_at | SPP1 | 1.318723271 | 0.02 | 7.27 |
| 182_at | ITPR3 | 1.107167336 | 0.006 | 7.27 |
| 32382_at | UPK1B | 0.731294678 | 0.047 | 7.16 |
| 863_g_at | SERPINB5 | 0.783530451 | 0.015 | 7.14 |
| 904_s_at | TOP2A | 0.971648429 | 0.02 | 7.12 |
| 40095_at | CA2 | 0.798857154 | 0.027 | 7.02 |
| 41294_at | KRT7 | 1.082553892 | 0.011 | 7.00 |
| 39951_at | PLS1 | 0.995091449 | 0.006 | 6.94 |
| 38051_at | MAL | 0.819842532 | 0.036 | 6.82 |
| 40726_at | KIF11 | 0.803689697 | 0.036 | 6.78 |
| 1148_s_at | — | 0.683569558 | 0.047 | 6.72 |
| 37920_at | PITX1 | 0.996497645 | 0.015 | 6.67 |
| 37117_at | ARHGAP8 | 1.129131077 | 0.002 | 6.65 |
| 38881_i_at | TRIM16 | 0.721698355 | 0.047 | 6.59 |
| 34251_at | HOXB5 | 1.219463307 | 0.002 | 6.52 |
| 41359_at | PKP3 | 1.047269618 | 0.004 | 6.50 |
| 40145_at | TOP2A | 0.961173129 | 0.02 | 6.48 |
| 37534_at | CXADR | 0.888147605 | 0.006 | 6.32 |
| 40303_at | TFAP2C | 0.948734146 | 0.004 | 6.30 |
| 31805_at | FGFR3 | 0.969764101 | 0.011 | 6.28 |
| 33245_at | MAPK13 | 0.877514586 | 0.011 | 6.27 |
| 885_g_at | ITGA3 | 0.702747685 | 0.036 | 6.19 |
| 34693_at | STHM | 0.872525584 | 0.008 | 6.15 |
| 38555_at | DUSP10 | 0.880305317 | 0.008 | 6.12 |
| 38418_at | CCND1 | 1.071102249 | 0.002 | 5.97 |
| 33730_at | RAI3 | 0.813298748 | 0.011 | 5.90 |
| 39109_at | TPX2 | 1.040973216 | 0.011 | 5.87 |
| 36658_at | DHCR24 | 1.122129795 | 0.004 | 5.81 |
| 35281_at | LAMC2 | 0.747766326 | 0.047 | 5.78 |
| 38749_at | MGC29643 | 0.683275086 | 0.036 | 5.77 |
| 1083_s_at | MUC1 | 0.746980491 | 0.027 | 5.75 |
| 40079_at | RAI3 | 0.709840659 | 0.02 | 5.73 |
| 2047_s_at | JUP | 0.815282235 | 0.011 | 5.62 |
| 32275_at | SLPI | 0.940625784 | 0.02 | 5.61 |
| 2020_at | CCND1 | 0.926408163 | 0.002 | 5.51 |
| 33324_s_at | CDC2 | 1.026683994 | 0.008 | 5.47 |
| 36863_at | HMMR | 0.96343264 | 0.006 | 5.46 |
| 1657_at | PTPRR | 0.764510362 | 0.02 | 5.41 |
| 37985_at | LMNB1 | 0.895475347 | 0.008 | 5.36 |
| 36497_at | C14orf78 | 0.942921564 | 0.008 | 5.33 |
| 2021_s_at | CCNE1 | 0.893228297 | 0.006 | 5.33 |
| 37890_at | CD47 | 0.775908217 | 0.015 | 5.33 |

TABLE 2-continued

Upregulated Genes Expressed At Least 5 Fold Higher In Ovarian Serous Papillary Carcinoma Compared With Normal Ovarian Epithelial Cells

| Probe Set | Gene Symbol | Score(d)(SAM) | p of WRS | Ratio OVA/NOVA |
|---|---|---|---|---|
| 40799_at | C16orf34 | 0.852774782 | 0.008 | 5.30 |
| 35309_at | ST14 | 0.852534105 | 0.008 | 5.30 |
| 1599_at | CDKN3 | 0.925527261 | 0.02 | 5.29 |
| 981_at | MCM4 | 1.058558782 | 0.006 | 5.28 |
| 32715_at | VAMP8 | 0.938171642 | 0.006 | 5.28 |
| 38631_at | TNFAIP2 | 0.72369235 | 0.015 | 5.26 |
| 34715_at | FOXM1 | 1.31035831 | 0.008 | 5.24 |
| 33448_at | SPINT1 | 0.924028022 | 0.015 | 5.21 |
| 419_at | MKI67 | 0.938133197 | 0.015 | 5.16 |
| 1651_at | UBE2C | 1.436239741 | 0.008 | 5.14 |
| 35769_at | GPR56 | 0.937347548 | 0.015 | 5.08 |
| 37310_at | PLAU | 0.885110741 | 0.036 | 5.08 |
| 36761_at | ZNF339 | 0.937123503 | 0.011 | 5.05 |
| 37343_at | ITPR3 | 1.001079303 | 0.003 | 5.05 |
| 40425_at | EFNA1 | 0.813414458 | 0.047 | 5.04 |
| 1803_at | CDC2 | 0.732852195 | 0.027 | 5.00 |

TABLE 3

Upregulated Genes Expressed At Least 5 Fold Higher In Normal Ovarian Epithelial Cells Compared With Ovarian Serous Papillary Carcinoma

| Probe Set | Gene Symbol | Score(d)(SAM) | p of WRS | Ratio NOVA/OVA |
|---|---|---|---|---|
| 39701_at | PEG3 | 1.991111245 | 0.006 | 113.32 |
| 32582_at | MYH11 | 1.921434447 | 0.002 | 67.31 |
| 39673_i_at | ECM2 | 1.740409609 | 0.011 | 53.54 |
| 37394_at | C7 | 1.597329897 | 0.02 | 50.45 |
| 37247_at | TCF21 | 2.261979734 | 0.002 | 39.29 |
| 1897_at | TGFBR3 | 1.648143277 | 0.003 | 38.12 |
| 36627_at | SPARCL1 | 1.610346382 | 0.008 | 37.84 |
| 37015_at | ALDH1A1 | 1.886579474 | 0.002 | 35.18 |
| 38469_at | TM4SF3 | 1.620821878 | 0.003 | 34.43 |
| 35717_at | ABCA8 | 1.709820793 | 0.008 | 33.92 |
| 32664_at | RNASE4 | 1.720857082 | 0.003 | 32.94 |
| 40775_at | ITM2A | 1.393751125 | 0.006 | 31.35 |
| 38519_at | NR1H4 | 1.431579641 | 0.004 | 27.02 |
| 37017_at | PLA2G2A | 1.263990266 | 0.011 | 26.68 |
| 36681_at | APOD | 1.44030134 | 0.008 | 26.04 |
| 34193_at | CHL1 | 1.738491852 | 0.006 | 25.97 |
| 34363_at | SEPP1 | 1.490374268 | 0.015 | 25.93 |
| 1501_at | IGF1 | 1.116943817 | 0.027 | 25.87 |
| 33240_at | SEMACAP3 | 1.818843975 | 0.003 | 25.54 |
| 36939_at | GPM6A | 0.924236354 | 0.047 | 25.47 |
| 614_at | PLA2G2A | 1.391395227 | 0.003 | 23.15 |
| 37407_s_at | MYH11 | 1.72766007 | 0.002 | 22.73 |
| 39325_at | EBAF | 1.248164036 | 0.02 | 22.49 |
| 767_at | — | 1.688001805 | 0.002 | 21.90 |
| 37595_at | — | 1.582101386 | 0.004 | 20.94 |
| 1290_g_at | GSTM5 | 1.383630361 | 0.003 | 20.84 |
| 34388_at | COL14A1 | 1.400078214 | 0.015 | 20.39 |
| 607_s_at | VWF | 1.314435559 | 0.002 | 19.05 |
| 37599_at | AOX1 | 1.669903577 | 0.003 | 17.61 |
| 41504_s_at | MAF | 1.463988429 | 0.008 | 16.40 |
| 41412_at | PIPPIN | 1.799353403 | 0.002 | 16.08 |
| 279_at | NR4A1 | 1.194733065 | 0.008 | 15.42 |
| 38427_at | COL15A1 | 1.570514035 | 0.002 | 15.38 |
| 41405_at | SFRP4 | 1.478603828 | 0.002 | 14.44 |
| 39066_at | MFAP4 | 1.91469237 | 0.004 | 14.26 |
| 1731_at | PDGFRA | 1.791307012 | 0.003 | 13.91 |
| 36595_s_at | GATM | 1.382271028 | 0.004 | 13.86 |
| 34343_at | STAR | 2.080476608 | 0.003 | 13.67 |
| 36917_at | LAMA2 | 1.359731285 | 0.006 | 13.51 |
| 38430_at | FABP4 | 1.054221974 | 0.02 | 13.05 |
| 36596_r_at | GATM | 1.22177547 | 0.008 | 12.67 |
| 35898_at | WISP2 | 1.276226302 | 0.004 | 12.55 |
| 36606_at | CPE | 1.608244463 | 0.003 | 12.30 |
| 32057_at | LRRC17 | 1.345223643 | 0.011 | 12.22 |

TABLE 3-continued

Upregulated Genes Expressed At Least 5 Fold Higher In Normal Ovarian Epithelial Cells Compared With Ovarian Serous Papillary Carcinoma

| Probe Set | Gene Symbol | Score(d)(SAM) | p of WRS | Ratio NOVA/OVA |
|---|---|---|---|---|
| 33431_at | FMOD | 1.516795166 | 0.003 | 12.17 |
| 34985_at | CILP | 0.905018335 | 0.02 | 11.53 |
| 755_at | ITPR1 | 1.433938835 | 0.002 | 11.06 |
| 1466_s_at | FGF7 | 1.184028604 | 0.027 | 11.00 |
| 36727_at | — | 0.98132702 | 0.036 | 10.96 |
| 1103_at | RNASE4 | 1.456068199 | 0.002 | 10.88 |
| 32666_at | CXCL12 | 1.342426238 | 0.006 | 10.72 |
| 914_g_at | ERG | 1.264721284 | 0.002 | 10.54 |
| 40698_at | CLECSF2 | 1.325237675 | 0.002 | 10.46 |
| 36873_at | VLDLR | 1.344197327 | 0.004 | 10.45 |
| 1090_f_at | — | 0.914708216 | 0.027 | 10.34 |
| 36042_at | NTRK2 | 0.950553444 | 0.02 | 10.32 |
| 36311_at | PDE1A | 1.356950738 | 0.004 | 10.21 |
| 41685_at | NY-REN-7 | 0.8848466 | 0.036 | 10.08 |
| 32847_at | MYLK | 1.545610138 | 0.002 | 10.00 |
| 35358_at | TENC1 | 1.539140855 | 0.003 | 9.97 |
| 32249_at | HFL1 | 1.257702238 | 0.02 | 9.86 |
| 36695_at | na | 1.452847153 | 0.003 | 9.82 |
| 1987_at | PDGFRA | 1.50655467 | 0.002 | 9.76 |
| 37446_at | GASP | 1.219014593 | 0.004 | 9.76 |
| 35752_s_at | PROS1 | 1.211272096 | 0.008 | 9.66 |
| 36533_at | PTGIS | 1.882348646 | 0.004 | 9.62 |
| 38886_i_at | ARHI | 1.127672988 | 0.02 | 9.59 |
| 36733_at | FLJ32389 | 1.420588897 | 0.011 | 9.57 |
| 38717_at | DKFZP586A0522 | 1.158933663 | 0.015 | 9.50 |
| 32551_at | EFEMP1 | 1.385495033 | 0.004 | 9.38 |
| 1968_g_at | PDGFRA | 1.364848071 | 0.003 | 9.31 |
| 33910_at | PTPRD | 1.129963902 | 0.008 | 9.20 |
| 32778_at | ITPR1 | 1.370809534 | 0.002 | 9.08 |
| 280_g_at | NR4A1 | 1.074894321 | 0.006 | 8.79 |
| 35389_s_at | ABCA6 | 1.209294071 | 0.011 | 8.79 |
| 32889_at | RPIB9 | 1.145333813 | 0.003 | 8.74 |
| 37248_at | CPZ | 1.238797022 | 0.002 | 8.69 |
| 39674_r_at | ECM2 | 0.874009817 | 0.027 | 8.67 |
| 33911_at | PTPRD | 1.099609918 | 0.02 | 8.66 |
| 35234_at | RECK | 1.407865518 | 0.008 | 8.58 |
| 32119_at | — | 1.153957574 | 0.011 | 8.57 |
| 35998_at | LOC284244 | 1.104281231 | 0.008 | 8.54 |
| 37279_at | GEM | 1.012760866 | 0.008 | 8.31 |
| 35702_at | HSD11B1 | 1.164189513 | 0.004 | 8.28 |
| 32126_at | FGF7 | 1.336918337 | 0.008 | 8.22 |
| 36867_at | — | 1.273166453 | 0.008 | 8.21 |
| 38653_at | PMP22 | 1.422063697 | 0.002 | 8.19 |
| 38875_r_at | GREB1 | 1.026886865 | 0.015 | 8.10 |
| 35366_at | NID | 1.483421362 | 0.002 | 8.10 |
| 34417_at | FLJ36166 | 0.783978445 | 0.047 | 7.98 |
| 37221_at | PRKAR2B | 0.927090765 | 0.036 | 7.91 |
| 39031_at | COX7A1 | 1.564725491 | 0.004 | 7.89 |
| 39757_at | SDC2 | 1.288106392 | 0.002 | 7.80 |
| 36629_at | DSIPI | 0.981563882 | 0.008 | 7.79 |
| 35390_at | ABCA6 | 1.026714913 | 0.036 | 7.79 |
| 39629_at | PLA2G5 | 1.405181995 | 0.002 | 7.70 |
| 40961_at | SMARCA2 | 0.996692724 | 0.015 | 7.68 |
| 719_g_at | PRSS11 | 1.399043078 | 0.002 | 7.65 |
| 40856_at | SERPINF1 | 1.077533093 | 0.008 | 7.55 |
| 37008_r_at | SERPINA3 | 1.134224016 | 0.002 | 7.53 |
| 33834_at | CXCL12 | 1.060878451 | 0.002 | 7.51 |
| 31880_at | D8S2298E | 1.177864913 | 0.002 | 7.45 |
| 37628_at | MAOB | 1.194963489 | 0.004 | 7.43 |
| 34853_at | FLRT2 | 1.250330254 | 0.027 | 7.41 |
| 38887_r_at | ARHI | 1.169953614 | 0.015 | 7.32 |
| 38220_at | DPYD | 1.024334451 | 0.02 | 7.26 |
| 1327_s_at | MAP3K5 | 0.891703475 | 0.02 | 7.23 |
| 1380_at | FGF7 | 1.096254206 | 0.004 | 7.14 |
| 37573_at | ANGPTL2 | 1.052539345 | 0.002 | 7.08 |
| 718_at | PRSS11 | 1.381205346 | 0.002 | 6.99 |
| 36712_at | — | 1.15195149 | 0.005 | 6.88 |
| 1709_g_at | MAPK10 | 1.160320795 | 0.002 | 6.85 |
| 39123_s_at | TRPC1 | 1.060327922 | 0.015 | 6.79 |
| 38627_at | HLF | 0.911787462 | 0.036 | 6.79 |
| 32076_at | DSCR1L1 | 1.127515982 | 0.002 | 6.77 |
| 36669_at | FOSB | 1.023057503 | 0.011 | 6.65 |
| 38194_s_at | IGKC | 1.239936045 | 0.015 | 6.64 |

TABLE 3-continued

Upregulated Genes Expressed At Least 5 Fold
Higher In Normal Ovarian Epithelial Cells Compared
With Ovarian Serous Papillary Carcinoma

| Probe Set | Gene Symbol | Score(d)(SAM) | p of WRS | Ratio NOVA/OVA |
|---|---|---|---|---|
| 39545_at | CDKN1C | 1.040717569 | 0.004 | 6.62 |
| 36993_at | PDGFRB | 1.384657766 | 0.004 | 6.60 |
| 35837_at | SCRG1 | 1.023840456 | 0.036 | 6.48 |
| 1507_s_at | EDNRA | 1.23933124 | 0.004 | 6.48 |
| 40488_at | DMD | 1.291791538 | 0.002 | 6.42 |
| 38364_at | — | 1.030881108 | 0.004 | 6.35 |
| 41424_at | PON3 | 0.946224951 | 0.036 | 6.32 |
| 32109_at | FXYD1 | 1.005577422 | 0.004 | 6.19 |
| 1182_at | PLCL1 | 1.097390316 | 0.002 | 6.17 |
| 31897_at | DOC1 | 1.533672652 | 0.003 | 6.13 |
| 37208_at | PSPHL | 1.007759699 | 0.015 | 6.08 |
| 36396_at | — | 1.009684807 | 0.015 | 6.07 |
| 41505_r_at | MAF | 1.116101319 | 0.006 | 6.06 |
| 37765_at | LMOD1 | 1.127716375 | 0.003 | 6.00 |
| 37398_at | PECAM1 | 0.970664041 | 0.008 | 5.98 |
| 41013_at | FLJ31737 | 1.036561659 | 0.003 | 5.98 |
| 39279_at | BMP6 | 1.106724571 | 0.002 | 5.93 |
| 1527_s_at | CG018 | 0.804755548 | 0.047 | 5.91 |
| 39038_at | FBLN5 | 1.279283798 | 0.004 | 5.89 |
| 32542_at | FHL1 | 1.134214637 | 0.002 | 5.88 |
| 38508_s_at | TNXB | 0.878513741 | 0.011 | 5.74 |
| 32696_at | PBX3 | 0.888011703 | 0.027 | 5.69 |
| 41796_at | PLCL2 | 0.857601993 | 0.02 | 5.68 |
| 34473_at | TLR5 | 0.871815246 | 0.027 | 5.67 |
| 661_at | GAS1 | 1.267909476 | 0.004 | 5.66 |
| 41449_at | SGCE | 1.050056933 | 0.004 | 5.65 |
| 35740_at | EMILIN1 | 1.366368794 | 0.011 | 5.58 |
| 37908_at | GNG11 | 0.989043327 | 0.004 | 5.43 |
| 37406_at | MAPRE2 | 1.265872665 | 0.002 | 5.41 |
| 33802_at | HMOX1 | 1.034088234 | 0.015 | 5.41 |
| 39106_at | APOA1 | 1.266005754 | 0.008 | 5.40 |
| 1771_s_at | PDGFRB | 1.336082701 | 0.006 | 5.39 |
| 39409_at | C1R | 1.05784087 | 0.011 | 5.39 |
| 32535_at | FBN1 | 1.422415283 | 0.006 | 5.35 |
| 37710_at | MEF2C | 0.98149558 | 0.011 | 5.35 |
| 37958_at | TM4SF10 | 1.293658009 | 0.003 | 5.35 |
| 33756_at | AOC3 | 0.829203515 | 0.02 | 5.29 |
| 36569_at | TNA | 0.926096917 | 0.006 | 5.25 |
| 39771_at | RHOBTB1 | 1.048906896 | 0.008 | 5.20 |
| 39852_at | SPG20 | 0.82401517 | 0.027 | 5.20 |
| 35168_f_at | COL16A1 | 1.509830282 | 0.011 | 5.18 |
| 33244_at | CHN2 | 0.92878389 | 0.015 | 5.18 |
| 35681_r_at | ZFHX1B | 1.170745794 | 0.006 | 5.14 |
| 2087_s_at | CDH11 | 1.656534188 | 0.008 | 5.12 |
| 40496_at | C1S | 0.973175912 | 0.011 | 5.10 |
| 41137_at | PPP1R12B | 1.12885067 | 0.008 | 5.07 |
| 39698_at | HOP | 0.797252583 | 0.011 | 5.05 |
| 38211_at | ZNF288 | 0.926263264 | 0.015 | 5.04 |
| 41839_at | GAS1 | 1.127093791 | 0.006 | 5.03 |
| 39979_at | F10 | 0.890787173 | 0.002 | 5.02 |
| 1135_at | GPRK5 | 1.150554994 | 0.002 | 5.01 |
| 479_at | DAB2 | 1.255638531 | 0.006 | 5.01 |

Example 4

Validation of the Microarray Data By Quantitative Real-Time PCR

Quantitative real time PCR assays were used to validate the microarray data. Four highly differentially expressed genes between normal ovarian epithelial cells and ovarian serous papillary carcinoma (i.e., TROP-1, CD24, Claudin-3 and Claudin-4) were selected for the analysis.

Quantitative real time PCR was performed with an ABI Prism 7000 Sequence Analyzer using the manufacturer's recommended protocol (Applied Biosystems, Foster City, Calif.). Each reaction was run in triplicate. The comparative threshold cycle ($C_T$) method was used for the calculation of amplification fold as specified by the manufacturer. Briefly, five mg of total RNA from each sample was reverse transcribed using SuperScript II Rnase H Reverse Transcriptase (Invitrogen, Carlsbad, Calif.). Ten ml of reverse transcribed RNA samples (from 500 ml of total volume) were amplified by using the TaqMan Universal PCR Master Mix (Applied Biosystems) to produce PCR products specific for TROP-1, CD24, Claudin-3 and Claudin-4. Primers specific for 18s ribosomal RNA and empirically determined ratios of 18s competimers (Applied Biosystems) were used to control for the amounts of cDNA generated from each sample.

Primers for TROP-1, claudin-3 and claudin-4 were obtained from Applied Biosystems as assay on demand products. Assays ID were Hs00158980_m1 (TROP-1), Hs00265816_s1 (claudin-3), and Hs00533616_s1 (claudin-4). CD24 primers sequences were as following: forward, 5'-CCCAGGTGTTACTGTMTTCCTCAA (SEQ ID NO.1); reverse, 5'-GMCAGCAATAGCTCMCAATGTAAAC (SEQ ID NO.2). Amplification was carried out by using 1 unit of polymerase in a final volume of 20 μl containing 2.5 mM $MgCl_2$. TaqGold was activated by incubation at 96° C. for 12 min, and the reactions were cycled 26-30 times at 95° C. for 1 min, 55° C. for 1 min, and 72° C. for 1 min, followed by a final extension at 72° C. for 10 min. PCR products were visualized on 2% agarose gels stained with ethidium bromide, and images were captured by an Ultraviolet Products Image Analysis System. Differences among ovarian serous papillary carcinoma and normal ovarian epithelial cells in the quantitative real time PCR expression data were tested using the Kruskal-Wallis nonparametric test. Pearson product-moment correlations were used to estimate the degree of association between the microarray and quantitative real time PCR data.

Figure 3:
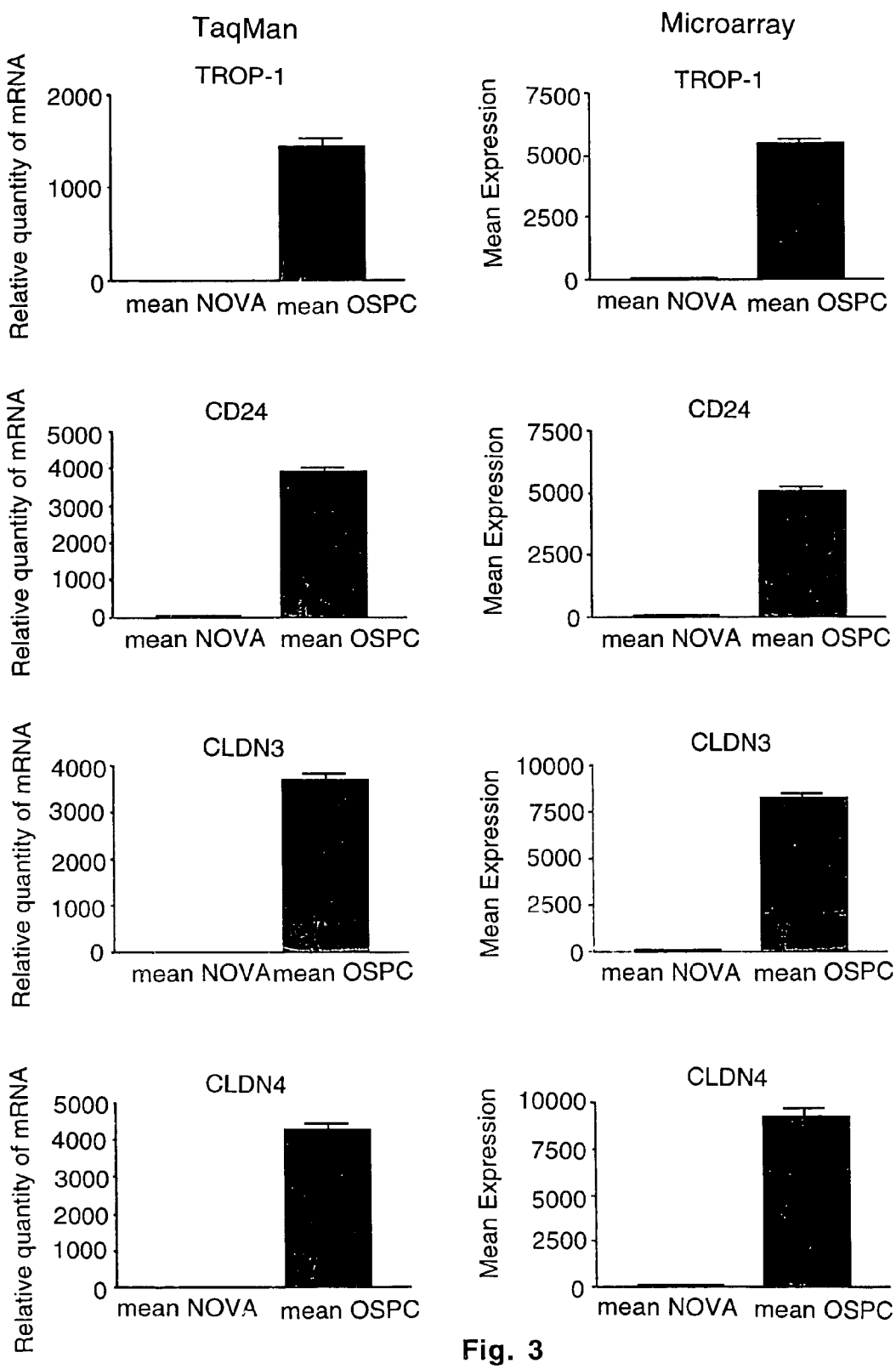
FIG. 3 shows quantitative real-time PCR and microarray expression analysis of TROP-1, CD24, claudin-3 and claudin-4 genes differentially expressed between ovarian serous papillary carcinomas cells and normal ovarian epithelial cells.

A comparison of the microarray and quantitative real time PCR data for these genes is shown in FIG. 3. Expression differences between ovarian serous papillary carcinoma and normal ovarian epithelial cells for TROP-1, (p=0.02), CD24 (p=0.004), claudin-3 (p=0.02), and claudin-4 (p=0.01) were readily apparent (Table 2 and FIG. 3). Moreover, for all four genes tested, the quantitative real time PCR data were highly correlated to the microarray data (p<0.001) (r=0.81, 0.90, 0.80 and 0.85, respectively). Thus, quantitative real time PCR data suggest that most array probe sets are likely to accurately measure the levels of the intended transcript within a complex mixture of transcripts.

Example 5

Flow Cytometry Analysis of TROP-1 and CD24 Expression

An important issue is whether differences in gene expression result in meaningful differences in protein expression. Because TROP-1/Ep-C A M gene encodes the target for the anti-Ep-CAM antibody (17-1A), Edrecolomab (Panorex), that has previously been shown to increase survival in patients harboring stage III colon cancer, expression of Ep-CAM protein by FACS analysis was analyzed on 13 primary cell lines (i.e., 10 ovarian serous papillary carcinoma cell lines and 3 normal ovarian epithelial cell lines). As positive controls, breast cancer cell lines (i.e., B7-474 and SK-BR-3, American Type Culture Collection) known to overexpress TROP-1/Ep-CAM were also studied.

Unconjugated anti-TROP-1/EP-CAM (IgG2a), anti-CD24 (IgG2a) and isotype control antibodies (mouse IgG2a) were all obtained from BD PharMingen (San Diego, Calif.). Goat anti-murine FITC labeled mouse Ig was purchased from Becton Dickinson (San Jose, Calif.). Flow cytometry was conducted with a FACScan, utilizing cellQuest software (Becton Dickinson).

Figure 4:
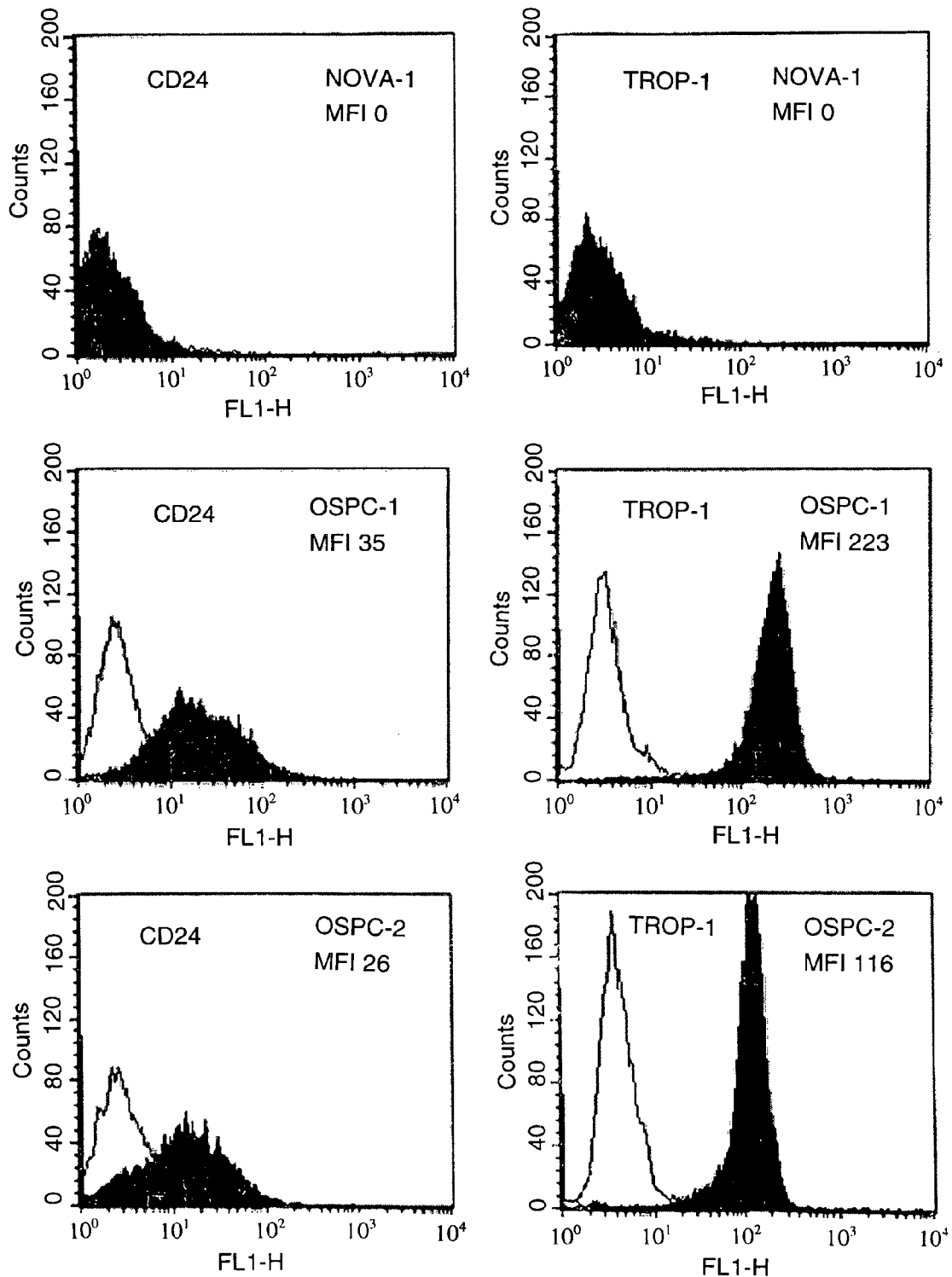
FIG. 4 shows representative FACS analysis of CD24 staining (left panel) and TROP-1/Ep-CAM staining (right panel) of 2 primary ovarian serous papillary carcinomas cell lines and 1 normal ovarian epithelial cell lines. Data with CD24 and TROP-1/Ep-CAM are shown in solid black while isotype control mAb profiles are shown in white. Both CD24 and TROP-1/Ep-CAM expression were significantly higher on ovarian serous papillary carcinomas cell lines compared to normal ovarian epithelial cell lines (p<0.001 by student t test).

High TROP-1/Ep-CAM expression was found on all ten primary ovarian serous papillary carcinoma cell lines tested (100% positive) with mean fluorescence intensity (MFI) ranging from 116 to 280 (FIG. 4). In contrast, primary normal ovarian epithelial cell lines were negative for TROP-1/Ep-CAM surface expression (p<0.001) (FIG. 4). Similarly, CD24 expression was found on all primary ovarian serous papillary carcinoma cell lines tested (100% positive) with mean fluorescence intensity (MFI) ranging from 26 to 55 (FIG. 4). In contrast, primary normal ovarian epithelial cell lines were negative for CD24 surface expression (p<0.005) (FIG. 4). These results show that high expression of the TROP-1/Ep-CAM and CD24 genes by ovarian serous papillary carcinoma correlate tightly with high protein expression by the tumor cells. Breast cancer positive controls were found to express high levels of TROP-1/Ep-CAM (data not shown).

Example 6

Immunohistochemical Analysis of TROP-1 and CD24 Expression

To determine whether the high or low gene expression and Ep-CAM and CD24 protein expression detected by microarray and flow cytometry are the result of a selection of a subpopulation of cancer cells present in the original tumor, or whether in vitro expansion conditions may have modified gene expression, immunohistochemical analysis of TROP-1/Ep-CAM and CD24 protein expression was performed on formalin-fixed tumor tissue from all uncultured primary surgical specimens. Study blocks were selected after histopathologic review by a surgical pathologist. The most representative hematoxylin and eosin-stained block sections were used for each specimen. Briefly, immunohistochemical stains were performed on 4 mm-thick sections of formalin-fixed, paraffin-embedded tissue. After pretreatment with 10 mM citrate buffer at pH 6.0 using a steamer, they were incubated with anti-Ep-CAM mAb (PharMingen) or anti-CD24 antibody (Neo Markers, Fremont, Calif.) at 1: 2000 dilution. Slides were subsequently labelled with streptavidin-biotin (DAKO, Glostrup, Denmark), stained with diaminobenzidine and counterstained with hematoxylin. The intensity of staining was graded as 0 (staining not greater than negative control), 1+ (light staining), 2+ (moderate staining), or 3+ (heavystaining).

Figure 5:
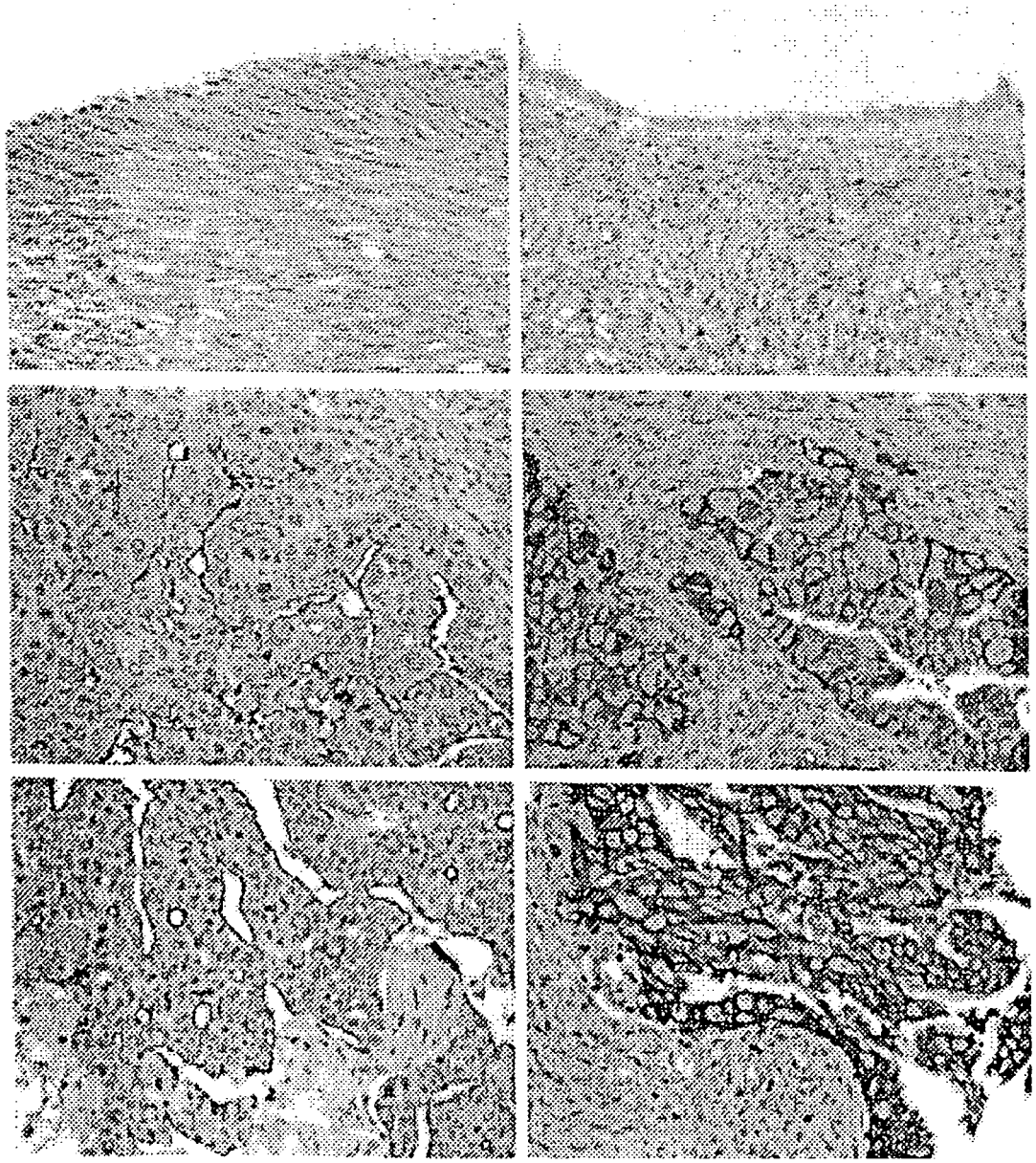
FIG. 5 shows representative immunohistochemical staining for CD24 (left panel) and Trop-1/Ep-CAM (right panel) on 2 paraffin-embedded ovarian serous papillary carcinomas (OSPC) cell lines and 1 normal ovarian epithelial cell (NOVA) specimen. NOVA1 (upper panel right and left) showed negative or light (1+) staining for both CD24 and Trop-1/Ep-CAM while OSPC 1 and OSPC 3 showed heavy apical membranous staining for CD24 (left panel) and strong membranous staining for TROP-1/Ep-CAM (right panel). Original magnification 400×

As shown in the left panel of FIG. 5, heavy apical membranous staining for CD24 protein expression was noted in all ovarian serous papillary carcinoma specimens that also overexpressed the CD24 gene and its gene product as determined by microarray and flow cytometry, respectively. In contrast, negative or low (i.e., score 0 or 1+) staining was found in all normal ovarian epithelial cell samples tested by immunohistochemistry. Similarly, as shown in the right panel of FIG. 5, heavy membranous staining for TROP-1/Ep-CAM protein expression (i.e., score 3+) was noted in all ovarian serous papillary carcinoma specimens that also overexpressed the TROP-1/Ep-CAM gene and its gene product as determined by microarray and flow cytometry, respectively. In contrast, negative or low (i.e., score 0 or 1+) staining was found in all normal ovarian epithelial cell samples tested by immunohistochemistry.

The following references were cited herein:

Eisen et al., Cluster analysis and display of genome-wide expression patterns. Proc Natl. Acad. Sci. USA 95:14863-68 (1998).
Fuchtner et al., Characterization of a human ovarian carcinoma cell line: UCI 101. Gynecol. Oncol. 48: 203-209 (1993).
Gamboa et al., Gynecol. Oncol. 58:336-343 (1995).
Hough et al., Cancer Res. 60:6281-7 (2000).
Ismail et al., Cancer Res. 60:6744-6749 (2000).
Riethmuller et al., J. Clin. Oncol. 16:1788-94 (1998).
Santin et al., Obstet. Gynecol. 96:422-430 (2000).
Tusher et al., Proc Natl. Acad. Sci. USA. 98: 5116-5121 (2001).
Zhan et al., Blood 99:1745-57 (2002).

What is claimed is:

1. A method of detecting ovarian serous papillary carcinoma in an individual, comprising the steps of:

examining a tumor sample from said individual by the expression level of a group of genes consisting of LAMC2, CLDN4, CLDN3, TACSTD1, TFAP2A, KRT6E, CDKN2A, UGT2B7, L1CAM, TACSTD2, LAD1, KIBRA, HBP17, PAX8, CLDN7, LAMA3, S100A1, CDH6, LCN2, FOLR3, DEFB1, BIK, FGF18, LAMB3, S100A2, WNT7A, GAL, CD24, EPHAT, HDAC9, DUSP4, ERBB3, CELSR1, NMU, ANXA3, KLK10, TRIM29, SERPINB2, ITGB4, CCNA1, CDH1, IL1RN, DKK1, DSP, TNNT1, ERBB2, SPP1, BUB1B, KLK6, BMP7, TSPAN-1, IMP-3, LISCH7, HOXB2, TTK, FGFR2, TGFA, NUP210, NFE2L3, CCND1, SFN, SRCAP, CCNE1, KRT6E, MAP17, MKI67, CDC6, PRSSB, SPP1, ITPR3, UPK1B, SERPINB5, TOP2A, CA2, KRT7, PLS1, MAL, KIF11, PITX1, ARHGAP8, TRIM16, HOXB5, PKP3, CXADR, TFAP2C, FGFR3, MAPK13, ITGA3, STHM, DUSP10, RAI3, TPX2, DHCR24, MGC29643, MUC1, JUP, SLPI, CDC2; HMMR, PTPRR, LMNB1, C14orf78, CD47, C16orf34, ST14, CDKN3, MCM4, VAMP8, TNFAIP2, FOXM1, SPINT1, MKI67, UBE2C, GPR56, RAU, ZNF339, ITPR3, and EFNA1; and performing hierarchical cluster analysis on the expression levels of said genes as compared to those in normal individual, wherein over-expression of said genes indicates that said individual has ovarian serous papillary carcinoma.

2. A method of detecting ovarian serous papillary carcinoma in an individual, comprising the steps of:

examining a tumor sample from said individual by the protein expression level of gene product in a group consisting of laminin, tumor-associated calcium signal transducer 1 (TROP-1/Ep-CAM), tumor-associated calcium signal transducer 2 (TROP-2), claudin 3, claudin 4, ladinin 1, S100A2, SERPINB2 (PAI-2), CD24, lipocalin 2, osteopontin, kallikrein 6 (protease M), kallikrein 10, matriptase and stratifin; and performing hierarchical cluster analysis on the expression levels of said genes as compared to those in normal individual, wherein over-expression of said genes indicates that said individual has ovarian serous papillary carcinoma.

3. The method of claim 1, wherein said gene expression is examined by DNA microarray.

4. The method of claim 1, wherein there is at least a 5-fold over-expression of said genes.

5. The method of claim 2, wherein said gene expression is examined by DNA microarray, flow cytometry or immunochemistry.

6. The method of claim 2, wherein there is at least a 5-fold over-expression of said genes.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<221> NAME/KEY: primer_bind
<223> OTHER INFORMATION: CD24 forward primer

<400> SEQUENCE: 1
cccaggtgtt actgtaattc ctcaa                                        25

<210> SEQ ID NO 2
<211> LENGTH: 27
<212> TYPE: DNA
<213> ORGANISM: Artificial Sequence
<220> FEATURE:
<221> NAME/KEY: primer_bind
<223> OTHER INFORMATION: CD24 reverse primer

<400> SEQUENCE: 2
gaacagcaat agctcaacaa tgtaaac                                      27